US012653704B2

(12) United States Patent
Cattaneo et al.

(10) Patent No.: US 12,653,704 B2
(45) Date of Patent: Jun. 16, 2026

(54) MEDICAL DEVICE, IN PARTICULAR A STENT

(71) Applicant: Acandis GmbH, Pforzheim (DE)

(72) Inventors: Giorgio Cattaneo, Karlsruhe (DE); Andreas Schüssler, Pfinztal (DE)

(73) Assignee: Acandis GmbH, Pforzheim (DE)

( * ) Notice: Subject to any disclaimer, the term of this patent is extended or adjusted under 35 U.S.C. 154(b) by 669 days.

(21) Appl. No.: 17/416,421

(22) PCT Filed: Dec. 11, 2019

(86) PCT No.: PCT/EP2019/084561
§ 371 (c)(1),
(2) Date: Jun. 18, 2021

(87) PCT Pub. No.: WO2020/126721
PCT Pub. Date: Jun. 25, 2020

(65) Prior Publication Data
US 2022/0071787 A1　　Mar. 10, 2022

(30) Foreign Application Priority Data

Dec. 21, 2018　(DE) ......................... 102018133285.8

(51) Int. Cl.
*A61F 2/90* (2013.01)
*A61L 31/02* (2006.01)
*A61L 31/18* (2006.01)

(52) U.S. Cl.
CPC .............. *A61F 2/90* (2013.01); *A61L 31/022* (2013.01); *A61L 31/18* (2013.01);
(Continued)

(58) Field of Classification Search
CPC .... A61F 2/915; A61F 2/90; A61F 2210/0076; A61F 2250/0032; A61F 2250/0098; A61L 31/022; A61L 31/18; A61L 2400/16
See application file for complete search history.

(56) References Cited

U.S. PATENT DOCUMENTS

2009/0177268 A1*　7/2009　Lundkvist ........ A61B 17/12118
140/71 C
2011/0160842 A1　6/2011　Mayer
(Continued)

FOREIGN PATENT DOCUMENTS

DE　202014102531　7/2014
DE　202015102114 U1　5/2015
(Continued)

OTHER PUBLICATIONS

Office Action dated Sep. 23, 2019, for German Patent Application DE 10 2018 133 285.8.
(Continued)

*Primary Examiner* — Suba Ganesan
(74) *Attorney, Agent, or Firm* — Cesari and McKenna, LLP

(57) ABSTRACT

The invention relates to a medical device, in particular a stent, having a radially self-expandable lattice structure (10) which is tubular at least in some sections and which is made of a single wire (11), which is interwoven with itself and which comprises a core material (11*a*) which is visible under X-ray and a superelastic jacket material (11*b*) and forms meshes (12) of the lattice structure (10). The invention is characterized in that a plurality of meshes (12) arranged directly adjacently in the circumferential direction of the lattice structure (10) form a mesh ring (13), and the lattice structure (10), in a fully self-expanded state, has an expansion diameter Dexp, the mesh ring (13) having a mesh number n, and the core material (11*a*) having a core diameter dKern, and the following being true for the core diameter dKern: dKern=f·(Dexp/n), with the following being true for a visibility factor f: 0.05≤f≤0.08.

19 Claims, 3 Drawing Sheets

(52) U.S. Cl.
      CPC ................. *A61F 2210/0076* (2013.01); *A61F 2250/0032* (2013.01); *A61F 2250/0098* (2013.01); *A61L 2400/16* (2013.01)

(56)                  References Cited

U.S. PATENT DOCUMENTS

| | | | | |
|---|---|---|---|---|
| 2017/0128242 A1* | 5/2017 | Ding | ......................... | A61F 2/90 |
| 2019/0240049 A1* | 8/2019 | Dawson | ................... | A61F 2/91 |

FOREIGN PATENT DOCUMENTS

| | | |
|---|---|---|
| DE | 202015105466 | 11/2015 |
| DE | 102016119369 A1 | 4/2017 |
| DE | 102015107291 A1 | 6/2017 |
| EP | 2762622 A2 | 8/2014 |
| EP | 2247268 | 5/2016 |

OTHER PUBLICATIONS

PCT Notification of Transmittal of the International Search Report and the Written Opinion of the International Searching Authority, or the Declaration, International Searching Authority, International Application No. PCT/US2019/084561, mailed Mar. 30, 2020, 4 pages.

\* cited by examiner

MEDICAL DEVICE, IN PARTICULAR A STENT

CROSS REFERENCE TO RELATED APPLICATIONS

This application is the National Stage of International Application No. PCT/EP2019/084561, filed Dec. 11, 2019, which claims the benefit of German Patent Application No. 102018133285.8 filed Dec. 21, 2018. The contents of both applications are hereby incorporated by reference in their entirety.

The invention relates to a medical device, more particularly a stent, in accordance with the introductory section of claim 1. A medical device of this type is known from EP 2 247 268 B1, for example.

The known medical device comprises a radially expandable lattice structure, which is tubular in some sections. The lattice structure is formed of a single wire which is interwoven with itself, through which meshes are formed. The wire of the lattice structure is made of a composite material, and in particular comprises a core material which is visible under X-ray and a superelastic jacket material.

The known medical device is designed as a stent. The known stent's core material, which is visible under X-ray, should allow the stent to be seen during X-ray monitoring. In contrast, the superelastic properties of the wire's jacket material should cause the stent to expand by itself, i.e. to be self-expandable.

As part of a further development of the known stent, it has been shown that it is difficult to achieve X-ray visibility of the lattice structure on the one hand, and good self-expandability on the other hand, particularly if the lattice structure is to be suitable for feeding into small, for example, intracranial blood vessels. In the case of insertion into small blood vessels it is necessary for the lattice structure to be compressed to a very small cross-sectional diameter. However, this is made more difficult by a high proportion of X-ray visible material, as such a material usually tends to deform plastically. During expansion of the lattice structure in the blood vessel, poor fitting of the lattice structure on the vascular wall can occur. Superelastic materials on the other hand, effect a high degree of compressibility and during the expansion ensure good vascular adaptation of the lattice structure.

For good visibility it would be expedient to increase the proportion of the wire's core material visible under X-ray. In this way, visibility of the entire lattice structure can be achieved that is useful in order to be able to check secure contacting of the lattice structure on a vascular wall over its entire length. However, core materials visible under X-ray do not have any superelastic properties and therefore make hardly any contribution to the expansion force that is required for the self-expansion of the lattice structure.

Particularly when inserting such a medical device into small blood vessels, preferably in the neurovascular field, such self-expandability is, however, desirable, so that a balloon catheter for expanding the lattice structure can be dispensed with. Such a balloon catheter would restrict the compressing of the lattice structure, so that the lattice structure cannot be inserted into particularly small blood vessels. A miniaturisation of the lattice structure, especially in its compressed state is therefore desirable. Further, subsequent manipulation by a balloon catheter increases the risk of injury.

A further factor that restricts the compressibility of the lattice structure is the wire diameter. This should not be too large, as otherwise, during compressing the wires come into contact early on, thereby preventing further compressing of the lattice structure.

Overall, it is therefore expedient to provide a lattice structure, the wire of which has as small a cross-sectional diameter as possible, but at the same time the ratio between the thickness of the jacket material and the core material is set in such a way that on the one hand good visibility under X-ray, and on the other hand good self-expandability are achieved. These properties are dependent on the geometry of the lattice structure, in particular the diameter of the lattice structure in the fully expanded state as well as on the number of meshes the lattice structure has distributed over its circumference.

Against this background, the object of the present invention is to propose a medical device, more particularly a stent, which has a high degree of visibility under X-rays at the same time as good self-expansion properties, wherein the medical device can be easily fed via small catheters, more particularly microcatheters, to the treatment location.

In accordance with the invention, this task is solved by the subject matter of patent claim 1.

The invention is based, in particular, on the idea of providing a medical device, more particularly a stent, with radially self-expandable lattice structure which is tubular at least in sections and is made of a single wire which is interwoven with itself, wherein the wire comprises a core material, which is visible under X-ray, and a superelastic jacket material element and forms meshes of the lattice structure. Several directly neighbouring meshes in the circumferential direction of the lattice structure form a mesh ring, wherein in a fully self-expanded state, the lattice structure has an expansion diameter $D_{exp}$, the mesh ring a mesh number n and the core material a core diameter $d_{core}$. According to the invention, for the core diameter $d_{core}$ the following applies:

$$d_{core} = f \cdot (D_{exp}/n)$$

According to the invention, for a visibility factor f, the following applies:

$$0.05 \leq f \leq 0.08$$

It has surprisingly been shown, that in the context of the above-described visibility factor, a ratio between the core diameter of the core material and the expansion diameter of the lattice structure comes about, which results in the lattice structure being particularly well visible in X-ray monitoring, at the same time as having a sufficiently great radial force in order to easily fulfil the desired self-expansion properties and also an overall wire diameter being able to be adhered to which makes good compressing of the lattice structure in small catheters, in particular microcatheters possible.

Taking into consideration the visibility factor determined in accordance with the invention, the direct connection between the core diameter and the expansion diameter makes it possible to select the correct quantity of core material visible under X-ray for different medical devices which differ from each other through the expansion diameter of their lattice structure. In other words, on the basis of the link between the core wire diameter and the expansion diameter envisaged by the invention, it is possible to select the best possible proportion of core material for different expansion diameters of lattice structures.

Generally, in the case of the invention, it is envisaged that the lattice structure is self-expandable. The wire forming the lattice structure therefore preferably has superelastic properties. The lattice structure can assume a fully self-expanded state by itself, in which no external forces act on the lattice structure. Rather, the internal self-expansion forces of the lattice structure result in the lattice structure expanding to a maximum cross-sectional diameter, the expansion diameter. This expansion diameter does not normally correspond to the cross-sectional diameter which the lattice structure assumes in the implanted state. For the implantation, it is usual to select a medical device, the cross-sectional diameter of which is between 10% and 35%, more particularly around 20%, greater than the cross-sectional diameter of a blood vessel into which the medical device is to be inserted. With this over-dimensioning, it is ensured that in the implanted state, the lattice structure exerts a sufficient radial force on the vascular walls so that the lattice structure remains firmly anchored at the place of implantation.

Through the effect of external forces, the lattice structure can be transferred into a compressed state. Here, the maximum compressed state is attained when, in practice, the lattice structure cannot be compressed further. This normally occurs when the wire sections that are arranged next to each other distributed around the circumference of the lattice structure, approach each other to such an extent that the wire sections come into contact and so mutually prevent further deformation. In other words, the fully compressed state is, in particular, reached, when the lattice structure is radially squeezed together so far that the meshes of the lattice structure are hardly recognisable as such, as the wire sections are directly in contact with each other. The circumference of the radially fully compressed lattice structure then essentially corresponds to the product of the sum of the wire sections arranged adjacently around the circumference and the wire diameter.

In the fully compressed state of the lattice structure, the lattice structure preferably assumes a cross-sectional diameter which is equal to or slightly smaller than an inner diameter of a catheter used for feeding the medical device into a blood vessel. In other words, the feeding diameter of the lattice structure is usually slightly larger than the diameter of the lattice structure in the fully compressed state. Here, it can be envisaged that lattice structures which have an expansion diameter of between 2.0 mm and 4.5 mm, more particularly between 2.5 mm and 4.5 mm, can be fed through a catheter with a catheter size of 2 French (inner diameter approximately 0.67 mm). Lattice structures with an expansion diameter of between 4.5 mm and 6.5 mm can be advantageously guided by a catheter with a catheter size of 2.5 French approximately 0.83 mm) to the treatment location. For lattice structures with an expansion diameter for 6.5 mm and more, it can be envisaged that they can be compressed to such an extent that they can be guided through a catheter with a catheter size of 3 French (inner diameter approximately 1 mm).

With the invention, generally it is preferably envisaged that the expansion diameter of the lattice structure is between 2.5 mm and 7 mm. Medical devices comprising lattice structures of this size are particularly suitable for the treatment of diseases in neurovascular blood vessels. In particular, such medical devices that are preferably designed as implants, especially as stents, are suitable for the treatment of diseases in intracranial blood vessels. Above all, in this way, intracranial aneurysms or stenoses, can be very well treated.

In a preferred form of embodiment of invention, it is envisaged that a width ratio $R_{GS}$ between the expansion diameter $D_{Exp}$ and the mesh number n in the case of an expansion diameter $D_{Exp}$ of between 2.5 mm and 3.5 mm, is between 0.3 mm and 0.5 mm, more particularly between 0.4 mm and 0.5 mm, preferably 0.42 mm. In the case of an expansion diameter $D_{Exp}$ of between 3.5 mm and 7 mm, the width ratio $R_{GS}$ between the expansion diameter $D_{Exp}$ and the mesh number n is preferably between 0.35 mm and 0.7 mm, more particularly between 0.38 mm and 0.7 mm, preferably 0.45 mm.

The width ratio $R_{GS}$ has a direct influence on the width of a mesh in the circumferential direction of the lattice structure. A high ratio between the expansion diameter and the mesh number leads to a greater width of the individual meshes. This has a negative effect on the stability of the lattice structure. Furthermore, a large mesh width can result, for example, in a coil inserted into an aneurysm that is to be held back by the lattice structure, easily passing through the meshes. Too small a ratio between the expansion diameter and the mesh number leads to a smaller mesh width, through which the ability to feed a lattice structure by way of a catheter can be made more difficult.

Surprisingly, it has been shown that the above values for the ratio between the expansion diameter and the mesh number offer a good compromise, so that the thus formed lattice structure on the one hand achieves a sufficiently high level of stability and, on the other hand, good feedability through a catheter. Moreover, by way of a thus formed lattice structure, embolic material, such as coils, can be easily placed through the meshes in an aneurysm. The thus formed medical devices are therefore well suited to being stably anchored in a blood vessel and at the same time to being guided to the treatment location through sinuous blood vessels. In addition, the thus formed lattice structures have a sufficiently small mesh width to efficiently hold back embolic material, for example, coils.

In preferred forms of embodiment, it is also envisaged that a braid angle $\alpha$ of the lattice structure is between 60° and 70°, more particularly 65°. The braid angle influences the mechanical expansion behaviour of the lattice structure. The braid angle also influences the bending flexibility and feedability of the device by way of catheters. For the treatment of intracranial blood vessels, a braid angle of between 60° and 70°, more particularly 65°, has been shown to be particularly preferable.

In the context of this application, the braid angle is denoted as the angle between the wire of a mesh and the longitudinal axis of the lattice structure. Specifically, in order to determine the braid angle, the longitudinal axis of the lattice structure is projected into the circumferential plane of the lattice structure and the angle to a wire extending helically over the outer surface of the lattice structure is then determined. In doing so, the braid angle must be distinguished from the mesh angle formed between two wire sections crossing each other. In the context of the present invention, the mesh angle corresponds to double the braid angle in each case.

In order to achieve good compressibility, it has been found to be particularly advantageous if the wire has a wire diameter $d_{wire}$ which in the case of an expansion diameter $D_{Exp}$ of between 2.5 mm and 3.5 mm, is between 40 μm and 55 μm, more particularly between 45 μm and 50 μm. In the case of an expansion diameter $D_{Exp}$ of between 3.5 mm and 7 mm, wire diameter $d_{wire}$ is preferably between 45 μm and 65 μm, more particularly 50 μm.

In connection with the number of meshes over the circumference of the lattice structure in the case of a predetermined expansion diameter and a predetermined braid angle of the lattice structure, the wire diameter also determines the ratio between the proportion of wire on the circumferential surface of the lattice structure in relation to the proportion of openings. This ratio between the proportion of wire material on the circumferential surface in relation to the entire outer surface of the lattice structure, is known as the braid density.

The ratio between the surface of the opening, i.e. the mesh surface, and the entire outer surface of the stent is known as porosity. The wire diameter has a direct influence on the braid density or porosity. Furthermore, the wire diameter influences the radial force of the lattice structure and its feedability by way of small catheters.

It has been shown that for the above-indicated expansion diameters, the cited wire diameters are particularly advantageous, i.e. on the one hand they provide a sufficiently great radial force and, on the other hand, make for good feedability by way of catheters. In addition, in the case of these wire diameters, a particularly advantageous braid density or porosity is achieved for the treatment of intracranial blood vessels.

The braid angle also has an influence on the porosity of the lattice structure. With the afore-mentioned preferred values for a braid angle in combination with the previously cited wire diameter values, a particularly advantageous porosity is achieved.

In order to ensure that the lattice structure of the medical device according to the invention has good self-expansion properties, it is advantageously envisaged that the jacket material of the wire has a thickness that is at least 10 μm.

It has been shown that irrespective of the expansion diameter of the lattice structure, a particular minimum thickness of the jacket material is required in order to achieve good self-expansion properties.

A minimum value of 10 μm as the thickness of the jacket material has proven to be particularly advantageous in order to achieve the desired self-expansion properties. The jacket material not only allows the self-expansion properties to be improved, but also forms good protection against corrosion and because of its hardness protects against wear.

In the case of wires that are thicker overall, a greater minimum thickness of the jacket material can be provided. For example, wires with a total thickness of at least 50 μm, more particularly at least 60 μm, can have a jacket material with a thickness of at least 15 μm. In order to also achieve good visibility properties of the lattice structure, it is advantageously envisaged that the volume of the core material constitutes a percentage proportion of the overall volume of the wire. In particular, it is envisaged that in the case of a visibility factor f of 0.05, the volume of the core material corresponds to between 13% and 32%, more particularly between 20% and 30%, more particularly between 25% and 30% of the overall volume of the wire. In the case of visibility factor f of 0.08 it is advantageously envisaged that the volume of the core material is between 25% and 45%, more particularly between 30% and 42%, more particularly between 35% and 40%, of the overall volume of the wire.

For feedability into blood vessels that are as small as possible, it is advantageous if the lattice structure can assume a fully compressed state in which the lattice structure has a compression diameter $D_{comp}$ which is at most 0.7 mm, more particularly at most 0.6 mm, more particularly at most 0.51 mm, more particularly at most 0.42 mm. This ensure that the lattice structure can be inserted through catheter systems with a catheter size between 2 French and 3 French.

The lattice structure preferably has closed loops at each of its axial ends. The closed loops have an atraumatic effect, i.e. they prevent injury to blood vessels when the lattice structure is being fed to the treatment location. Preferably the closed loops are formed in that the single wire, which forms the lattice structure, is deflected and returned at each of the longitudinal ends. In a central area of the lattice structure, the wire ends of the single wire can then be connected to each other, by means of a crimp sleeve, for example. The crimp sleeve can be of a material visible under X-ray.

In order to achieve good anchoring of the lattice structure in the blood vessel, and to avoid tapering of the lattice structure at its longitudinal ends, it is advantageously envisaged that the longitudinal ends of the lattice structure are widened in the shape of a funnel. In particular, this prevents the longitudinal ends bending inwards in the implanted state and the loops of the lattice structure disrupting the blood flow.

For good visibility of the medical device under X-ray, it has proven to be particularly advantageous if the core material of the wire is made of platinum or a platinum alloy. Alternatively, the core material can be made of tantalum or a tantalum alloy. Other suitable materials are gold, silver, tungsten and/or niobium or alloys thereof.

The jacket material is preferably made of a nickel-titanium alloy, more particularly nitinol. In a preferred variant, the nickel-titanium alloy can have a nickel proportion of 50.8 atomic percent.

The surface of the jacket material can comprise an oxide layer. More particularly, an oxide layer with a layer thickness of between 50 nm and 500 nm, more particularly between 100 nm and 400 nm, more particularly between 200 nm and 350 nm can be provided. The oxide layer makes it possible for the wire sections to easily slide onto each other and thereby promotes the self-expansion properties of the lattice structure.

One aspect of the invention envisages the provision of a set with an above-described medical device and a catheter, wherein in the compressed state the medical device can be arranged in the catheter in a longitudinally displaceable manner. The set can also comprise a transport wire, wherein the medical device can be, or is, detachably or firmly connected to the transport wire. Preferably, the catheter contained in the set has an inner diameter which is at most 0.7 mm, more particularly at most 0.6 mm, more particularly at most 0.51 mm, more particular at most 0.42 mm.

The invention will be described below in more detail with the aid of an example of embodiment with reference to the accompanying schematic drawings. In these:

Figure 1:
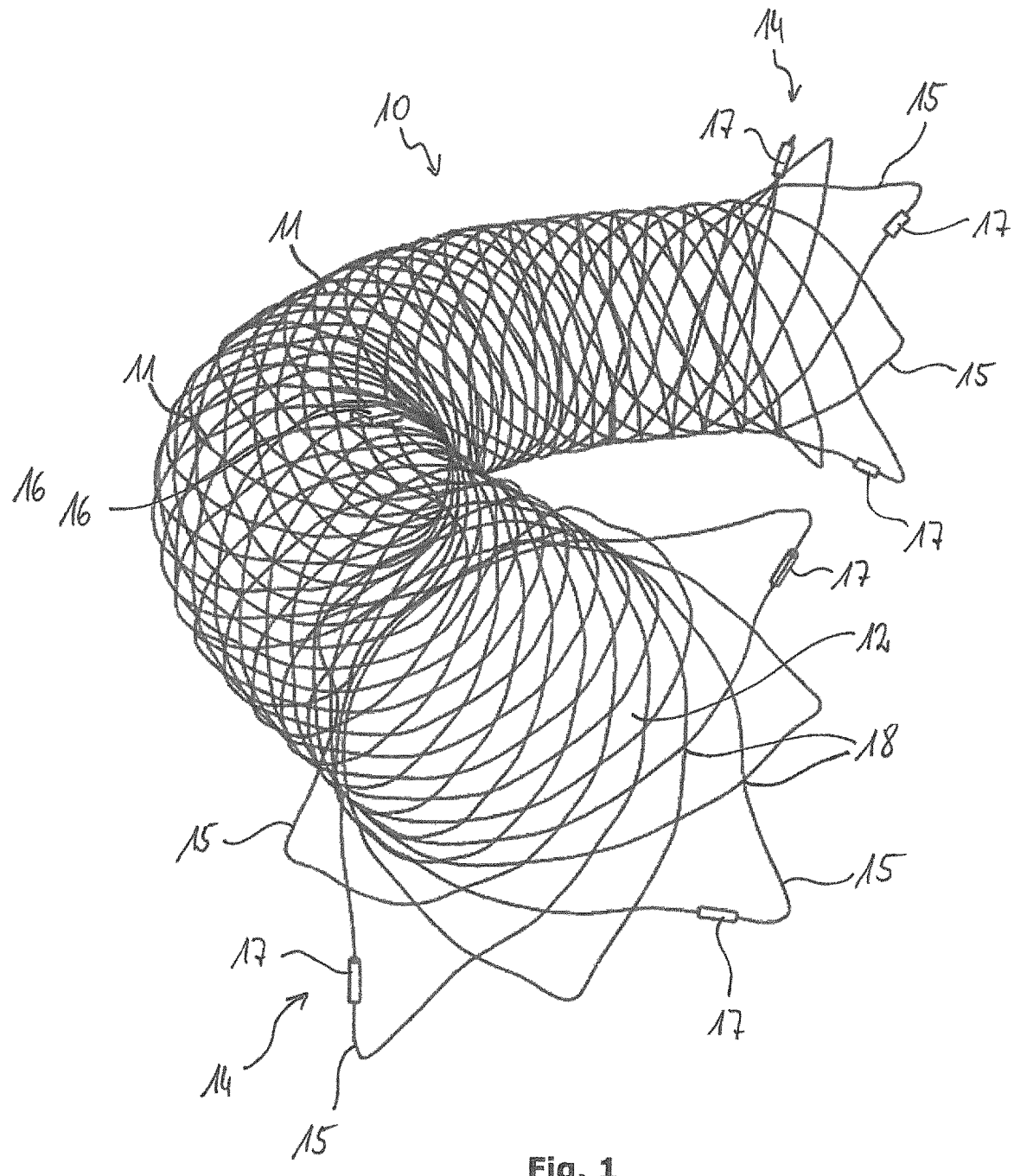
FIG. 1 shows a perspective view of a medical device according to the invention in accordance with the preferred example of embodiment.

The medical device according to the invention which is shown in the example of embodiment in figures, involve, in particular, a stent which is suitable for treatment in intracranial blood vessels.

Fundamentally, the medical device can be in the form of a medical instrument or a medical implant. In all cases, it is preferably envisaged that the medical device can be guided in a minimally invasive manner by way of catheter to a treatment location, in particular within a blood vessel. As a medical instrument, the device according to the invention can, for example, constitute a thrombectomy device. The thrombectomy device can have a lattice structure 10, which is tubular at least in sections. At a distal end, the lattice structure 10 can be closed, in order to thus form a catching basket which can collect the thrombus material. The thrombectomy device is preferably firmly connected to a transport wire and for the treatment of a vascular disease does not remain in the body permanently. Instead, the thrombectomy device, like other medical instruments, is only used for short time.

In contrast, medical implants remain permanently at their treatment location. Such implants are, in particular, stents which are inserted into blood vessels for the treatment of aneurysms. The stents can also be used for other things. For example, such stents can also be used to treat stenoses or plaque deposits in blood vessels.

The stent shown in attached drawings is preferably suitable for the treatment of aneurysms in intracranial blood vessel.

The stent comprises a tubular, radially expandable lattice structure 10 which is formed of a single wire 11 which is interwoven with itself. At each of the longitudinal ends 14 of the lattice structure 10, the wire 11 forms loops 15. The two ends of the wire are brought together in the middle of the lattice structure 10 and are coupled to each other with a connection element 16. The connection element 16 can comprise, or be made of, a material which is visible under X-rays.

The lattice structure 10 is greatly compressible and can thus be fed to the treatment location by way of small catheters. As can also be easily seen in FIG. 1, the lattice structure 10 has a high degree of bending flexibility so that feeding into, and anchoring in, very sinuous blood vessels is easily possible.

Figure 2:
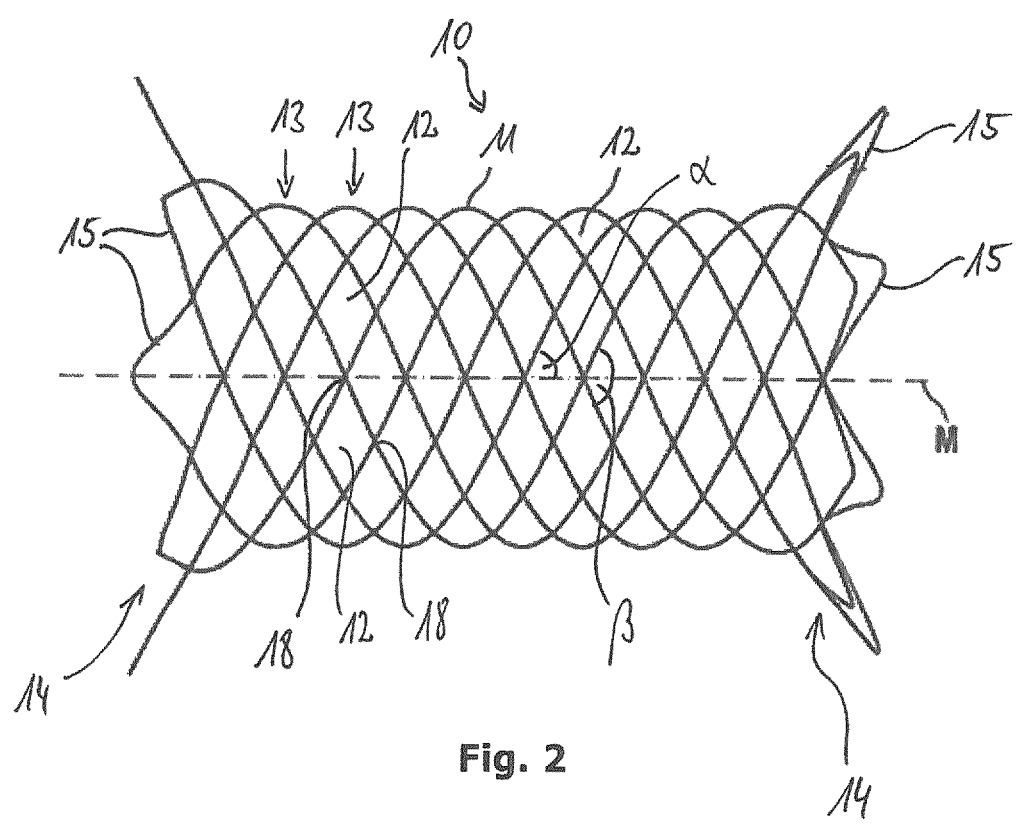
FIG. 2 shows a side view of the device according to FIG. 1.

Furthermore, it can be easily seen in FIGS. 1 and 2 that the lattice structure 10 is widened in a funnel shape at the longitudinal ends 14. Specifically, at its longitudinal ends, the lattice structure 10 has loops 15 widened in a funnel shape or opening up radially outwards.

In order to make the longitudinal ends 14 easily visible in X-ray monitoring, X-ray marker sleeves 17 are provided which are applied to the wire 11 in the area of a loop 15. Specifically, the loop 15 has a vertex and two arms, wherein the X-ray marker sleeve 17 is arranged on one of the arms. In particular, the X-ray marker sleeve 17 can be crimped onto the arm. In the shown example of embodiment, it is envisaged that only every second loop 15 carries an X-ray marker sleeve 17.

Overall, it is envisaged that three X-ray markers sleeves 17 are arranged on each longitudinal end 14. This ensures that the longitudinal ends 14 of the lattice structure 10 are easily seen in X-ray monitoring even if the lattice structure 10 has become twisted. At the same time, it makes sense to limit the number of X-ray markers sleeves 17 per longitudinal end 14 as in this way good compressibility of the lattice structure 10 is achieved. A greater number of X-ray marker sleeve 17 could lead to the X-ray marker sleeves 17 blocking each other during compressing and thereby prevent further compression of the lattice structure 10.

As can be easily seen, particularly in FIG. 2, the lattice structure 10 comprises several meshes 12, which seen in the circumferential direction of the lattice structure 10 each form mesh rings 13. A mesh ring 13 is formed from several meshes 12 which are arranged directly adjacent to each other in the circumferential direction of the lattice structure. The individual meshes are separated from each other by intersections 18 of the wire 11.

The lattice structure is built up of several mesh rings 13 arranged directly adjacent to each other in the longitudinal direction of the lattice structure 13. It is preferable if each mesh ring 13 has an even number of meshes 12. In particular, the mesh ring 13 can comprise 6, 8, 12, 14 or 16 meshes.

The lattice structure 10 is self-expandable and expends radially by itself without the effect of external forces. In this state, without forces acting on it, the lattice structure 10 assumes the expansion diameter $D_{exp}$. In a fully expanded state, the lattice structure 10 consequently has the expansion diameter $D_{exp}$.

By contrast, an external force effect is required to transfer the lattice structure 10 into a compressed state. A state in which the lattice structure 10 assumes its smallest possible diameter is the fully compressed state. In this fully compressed the lattice structure 10 has a compression diameter $D_{comp}$. During compression of the lattice structure 10, the width of a mesh 12 reduces in the circumferential direction of the lattice structure 10. This reduction in width takes place until the wire sections, which define the mesh 12, are in contact with each other. Through this, the wire 11 blocks further compression of the lattice structure 10. For mechanical and/or geometric reasons the lattice structure 10 cannot be compressed to any desired extent, but assumes a minimum diameter, as of which no further compression is possible. This state constitutes the fully compressed state in which the lattice structure 10 has a compression diameter $D_{comp}$.

A compression diameter $D_{comp}$ which is as small as possible is expedient in order to be able to feed the lattice structure 10 to the treatment location through catheters that are as small as possible. In particular, it is envisaged that the lattice structure can be compressed in such a way, or can assume a compression diameter $D_{comp}$ such that the lattice structure can be guided to the treatment location via a catheter with an inner diameter of at most 3 French, more particularly 2.5 French, more particularly at most 2 French. More specifically, the lattice structure can assume a compression diameter $D_{comp}$ which is at most 0.7 mm, more particularly 0.6 mm, more particularly at most 0.51 mm, more particularly at most 0.42 mm.

The wire 11, which forms the lattice structure 10, is preferably designed as a composite wire. For this, the wire comprises a core material 11*a*, which is visible under X-ray, and a superelastic jacket material 11*b*. The core material 11*a* can, in particular, comprises platinum, a platinum alloy, tantalum and/or a tantalum alloy. In all events, the core material 11*a* is preferably characterised by increased visibility under X-ray radiation. This means that the entire lattice structure 10 can be easily seen by the surgeon during the implantation.

The jacket material 11*b* on the other hand, serves to provide the self-expansion properties of the lattice structure 10. For this, the jacket material 11*b* has superelastic properties. More particularly, the jacket material can be formed by a shape-memory material, which under the influence of the ambient temperature assumes a previously imparted shape. A shape-memory material of this type, can, in particular, before formed of a nickel-titanium alloy. Preferably the jacket material 11*b* is adapted in such a way that on reaching the body temperature of a human it pushes the lattice structure 10 into the fully expanded state.

Depending on the desired size of the lattice structure 10 of the medical device, in particular the stent, it expedient to adapt the diameter of the core material, the core diameter $d_{core}$ accordingly. More particularly, the self-expansion properties, the compressibility and the visibility under X-ray of the lattice structure 10 should be matched to each other in the best possible way. It has been shown that for different expansion diameters $D_{exp}$, a core diameter $d_{core}$ that results from the product of the quotient of the expansion diameter $D_{exp}$ and the mesh number n of the meshes 12 of the mesh ring 13 as well as a visibility factor f is advantageous. The visibility factor f is preferably at least 0.05 and at most 0.08.

It has been specifically shown that a core diameter calculated on the basis of the above parameters results in good visibility of the lattice structure 10 under X-ray, wherein the lattice structure 10 still has good self-expanding properties and can be compressed to a small compression diameter. The equation $$d_{core}=f\cdot(D_{exp}/n)$$

applies for lattice structures 10 with different expansion diameters $D_{exp}$.

More particular, calculating the core diameter $D_{core}$ using this equation results in good parameters for lattice structures 10 which have an expansion diameter $D_{exp}$ between 2.5 mm and 7 mm. Such lattice structures 10 are, in particular, suitable for use in intracranial blood vessels.

In order to achieve good compressibility of the lattice structure 10, it is particularly advantageous, if as in the case of the shown examples of embodiment, the wire 11 has a wire diameter $d_{wire}$ which is at most 65 µm more particularly at most 60 µm, more particularly at most 55 µm, more particularly at most 40 µm. The wire 11 can have a wire diameter $d_{wire}$ which is between 40 µm and 50 µm, preferably between 45 µm and 50 µm. Specifically, the wire diameter $d_{wire}$ can be 40 µm or 45 µm or 50 µm. Such thin wires allow a particularly high degree of compression of the lattice structure 10, thus also leading to a very small compression diameter $D_{comp}$. This ensures that the lattice structure 10 can be easily fed to the treatment location through small catheters.

Figure 4:
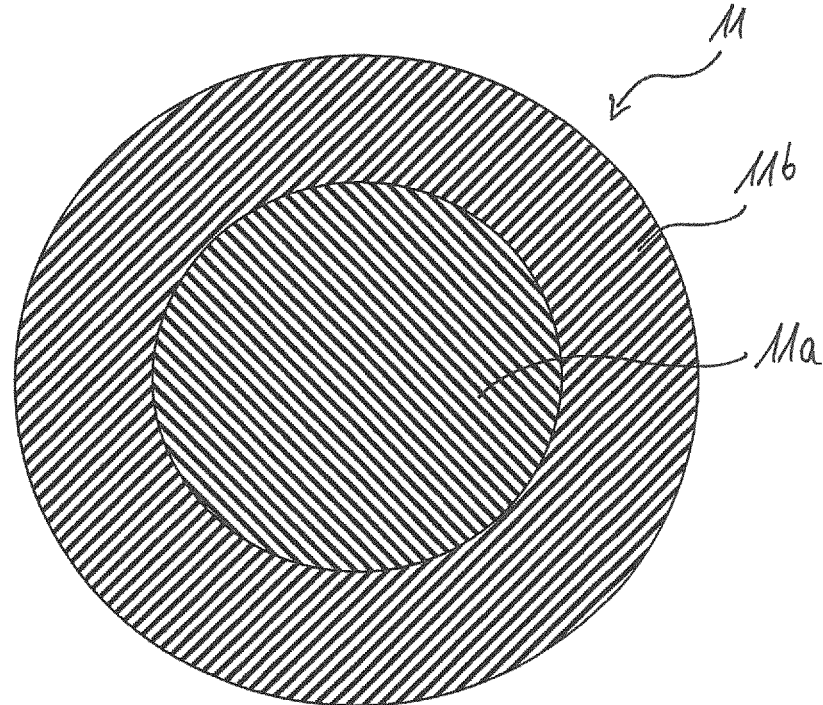
FIG. 4 shows a schematic view of a cross-sectional profile of the wire of the medical device according to FIG. 1.

It has also been shown that for the self-expansion properties of the lattice structure 10, a wire 11 with a jacket material thickness h of at least 10 µm is advantageous. Thus, in the case of a wire diameter $d_{wire}$ of 40 µm a maximum possible core diameter of 20 µm results. In FIG. 4 it can be clearly seen that through a thickness h of 10 µm for the jacket material 11*b*, with a wire diameter $d_{wire}$ of 40 µm for the core material 11*a*, a core diameter $d_{core}$ of at most 20 µm remains.

The best possible maximum wire diameter $d_{wire}$ is determined on the one hand by the expansion diameter $D_{exp}$ and, on the other hand, by the mesh number n of the respective lattice structure 10. For lattice structures 10 with an expansion diameter $D_{exp}$ between 2.5 mm and 7 mm, wire diameters $D_{wire}$ between 40 µm and 65 µm, more particularly between 40 µm and 60 µm, have proven to be advantageous.

From the aforementioned geometric specifications, the percentage proportion of the volume of core material 11*a* in relation to the overall volume of the wire 11 can be calculated. This essentially corresponds to the quotient between the square of the ratio of the product from the visibility factor f and the mesh width b to the square of the wire diameter $d_{wire}$. The mesh width b results from the ratio between the expansion diameter $D_{exp}$ and the mesh number n. Specifically, the volume proportion φ of the core material 11*a* can be calculated as follows:

$$\varphi=(f\cdot D_{exp}/n)^2/d_{wire}^2$$

Expressed in percent, in the case of a visibility factor f of 0.05, the percentage by volume of the core material 11*a* in relation to the overall volume of the wire 11 is preferably between 13% and 32%, more particularly between 20% and 30%, more particularly between 25% and 30%.

With a visibility factor f of 0.08, the percentage by volume φ of the core material 11*a* in relation to the overall volume of the wire 11 is preferably between 25% and 45%, more particularly between 30% and 42%, more particularly between 35% and 40%.

Figure 3:
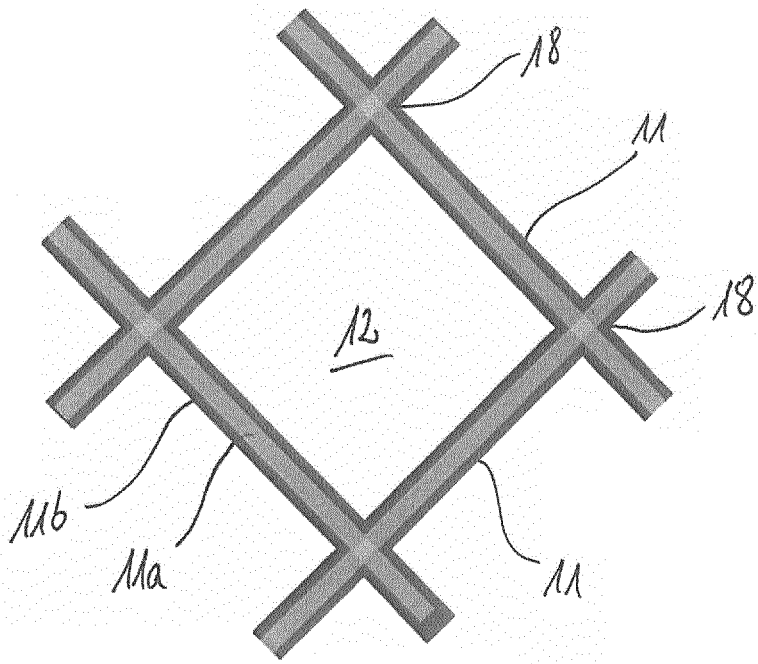
FIG. 3 shows a schematic view of a mesh of the lattice structure of the medical device according to FIG. 1.

In FIG. 3, a section of the lattice structure 10 of the medical device or the stent according FIG. 1 is shown. Specifically, FIG. 1 shows a single mesh 12 of the lattice structure 10, which is delimited by several wire sections of the wire 11. As is usual in the case of lattice structures 10, the mesh 12 is rhombus-shaped.

In FIG. 3 it is again clearly shown how the wire 11 is designed as a composite wire. In particular for illustration purposes, it is shown that the core material 11*a* extends through the wire 11 and is surrounded by the jacket material 11*b*. In X-ray monitoring, the core material 11*a* is visible in particular, wherein the X-ray density is particularly high in the area of the intersections 18 of the wire 11. The intersections 18 are therefore particularly well seen during X-ray monitoring.

The braid angle α of the lattice structure 10 in the shown forms of embodiment is preferably between 60 and 70 degrees, preferably 65 degrees, wherein a tolerance of ±3 degrees can be envisaged. In the context of the present invention, the braid angle α is considered as the angle formed between a longitudinal axis M of the lattice structure 10 and the wire 11. The wire 11 is helically wound around the longitudinal axis M.

For clarification, the braid angle α is illustrated in FIG. 2. It is also conceivable that because of the rhomboid shape of the individual meshes 12, the braid angle α essentially corresponds to half the entire mesh angle β. The mesh angle β is formed between two intersecting wire sections of the wire 11, wherein these wire sections are arranged next to each other in the circumferential direction.

In general, the invention is based on the following considerations:

For a product series of medical devices, more particularly stents, the lattice structure of which is essentially configured in the same way, though the individual products differ in terms of their expansion diameter $D_{exp}$, it is expedient to increase the mesh number n of the individual mesh rows 13 with increasing expansion diameter $D_{exp}$.

The width b of an individual mesh can generally be calculated from the expansion diameter $D_{exp}$ and the mesh number n is as follows:

$$b=\pi\cdot D_{exp}/n$$

In the context of this application, the ratio $D_{exp}/n$ between the expansion diameter $D_{exp}$ and the mesh number n, is designated as the width ratio $R_{GS}$.

With a high width ratio $R_{GS}$, the individual meshes are comparatively wide. This has the drawback that embolic material, such as coils in an aneurysm, can only be held back by the lattice structure 10 with difficulty.

Furthermore, a large mesh width b negatively affects the stability of the lattice structure 10.

By contrast, with a small width ratio $R_{GS}$, a small mesh width b is produced. Through this the lattice structure 10 becomes less flexible, so that navigation of the medical device through a catheter becomes more difficult. A small mesh width b also means that microcatheters, which are used to insert coils into an aneurysm, can only be fed through the meshes with difficulty.

It is therefore expedient to arrive at a mesh width b which achieves a compromise between the stability and good navigability of the lattice structure 10. It has been shown that a width ratio $R_{GS}$ in a range of 0.4 mm to 0.5 mm leads to good results. Taking into account the circle constant n, this results in a preferred mesh width b of between 1.25 mm and 1.6 mm.

In the case of an expansion diameter $D_{exp}$ of 2.4 mm, a width ratio $R_{GS}$ of between 0.3 mm and 0.45 mm, more particularly between 0.4 mm and 0.45 mm, preferably 0.42 mm, is preferred.

Lattice structures 10 with an expansion diameter $D_{exp}$ of more than 2.5 mm, preferably have a width ratio $R_{GS}$ of between 0.35 mm and 0.7 mm, more particularly between 0.38 mm and 0.6 mm. More specifically, the width ratio $R_{GS}$ can be between 0.35 and 0.7 mm if the lattice structure 10 has an expansion diameter $D_{exp}$ of between 2.5 mm and 3.5 mm. Lattice structures 10 with an expansion diameter $D_{exp}$ between 3.5 mm and 7 mm preferably have a width ratio $R_{GS}$ of between 0.35 mm and 0.6 mm.

The braid angle $\alpha$ influences the mechanical expansion behaviour, the flexibility and feedability of the medical device. A braid angle $\alpha$ between 60° and 70°, preferably 650 has proven to be well suited for the treatment of intracranial blood vessels by way of medical devices with a lattice structure 10 having an expansion diameter $D_{exp}$ of between 2.5 mm and 7 mm.

A predetermined width ratio $R_{GS}$ and consequently a predetermined mesh width b as well as a predetermined braid angle $\alpha$ result in a rhomboid shape and size of the mesh 12, from which, in combination with the wire diameter $d_{wire}$, a braid density or porosity results. The braid density indicates the proportion of the entire outer surface of the lattice structure that is formed by the wire 11, i.e. less the opening surface of the meshes 12. The porosity on the other hand, indicates the proportion of the overall outer surface of the lattice structure formed by the sum of the opening surfaces of the meshes 12. The width ratio $R_{GS}$ also influences the maximum incircle diameter of the mesh 12, which is also known as "pin opening".

Together with the braid angle $\alpha$ and the width ratio $R_{GS}$, the wire diameter $d_{wire}$ influences the braid density and the porosity of the lattice structure 10 and also affects the radial force and the feedability of the medical device. The following wire diameters $d_{wire}$ have proven to be advantageous for different expansion diameters $D_{exp}$:

In the case of an expansion diameter $D_{exp}$ of 2.5 mm the wire diameter $d_{wire}$ is preferably between 40 μm and 50 μm, more particularly between 45 μm and 50 μm.

In the case of an expansion diameter $D_{exp}$ between 2.5 mm and 4.5 mm the wire diameter $d_{wire}$ is preferably between 45 μm and 60 μm, more particularly 50 μm.

In the case of an expansion diameter $D_{exp}$ between 4.5 mm and 6 mm the wire diameter $d_{wire}$ is preferably between 50 μm and 65 μm, more particularly 55 μm.

In the case of an expansion diameter $D_{exp}$ between 6 mm and 7 mm the wire diameter $d_{wire}$ is preferably between 50 μm and 65 μm, more particularly 60 μm.

The length of the lattice structure 10 is preferably between 10 mm and 50 mm.

For good visibility under X-ray, the wire 11 has an X-ray visible core material 11a with a core diameter $d_{core}$. When selecting the core diameter $d_{core}$, the size of the individual meshes 12 plays an important role. The wider and longer the meshes 12, the lower is the braid density of the lattice structure 10. A higher core diameter $d_{core}$ is required in order to easily see the wire 11 during X-ray monitoring.

More particularly, the mesh width b influences the distance between the intersections 18 of a mesh row 13. At the intersections 18, sections of the wire 11 overlap and thereby form areas with an increased X-ray density. The more the intersections 18 are distanced from each other, the greater the core diameter $d_{core}$ should be in order to ensure good visualisation of the lattice structure 10. More particularly, through a high number of intersections, not only is the surface of the lattice structure 10 easily seen, but also the shape of the lattice structure 10, adapting to the vascular wall.

The width ratio $R_{GS}$ determines the density of the intersections 18 of a mesh row 13. The smaller the width ratio $R_{GS}$, the smaller is the distance between the intersections 18 and the higher the braid density of the lattice structure 10.

With a high width ratio $R_{GS}$, a relatively large core diameter $d_{core}$ is expedient. For a small width ratio $R_{GS}$, an accordingly smaller core diameter $d_{core}$ is sufficient.

It has been shown that a ratio between the core diameter $d_{core}$ and the width ratio $R_{GS}$ of between 0.05 und 0.08 leads to good results. In the context of the present application, the aforementioned ratio produces the thus designated visibility factor f.

In the case of a visibility factor f of 0.05, with a width ratio $R_{GS}$ of between 0.4 and 0.5 mm, an advantageous core diameter $d_{core}$ of between 20 μm and 25 μm results. For a greater width ratio $R_{GS}$, the core diameter $d_{core}$ can increase to up to 30 μm, more particularly up to 35 μm.

In the case of a visibility factor f of 0.08, with a width ratio $R_{GS}$ between 0.4 mm and 0.5 mm, an advantageous core diameter $d_{core}$ of between 33 μm and 40 μm results. For a smaller width ratio $R_{GS}$, the core diameter $d_{core}$ can be reduced to a value of between 30 μm and 25 μm, more particularly specifically to 30 μm, in particular 25 μm.

In order to assume sufficient torsion resistance and thereby a suitable restoring force during a spring-like deformation of the wire 11, it is advantageous if the jacket material 11b has a thickness that is at least 10 μm. In the case of a maximum wire diameter $d_{wire}$, this results in an upper limit for the core diameter $d_{core}$ of 40 μm.

With one of 2.5 mm and a preferred wire diameter $d_{wire}$ of 40 μm, the core diameter $d_{core}$ must not be greater than 20 μm, as otherwise the proportion of jacket material 11b would be too low. In order to achieve this, a visibility factor of 0.05 should be selected. With a larger expansion diameter $D_{exp}$, the preferred wire diameter $d_{wire}$ is at least 50 μm. For such lattice structures 10, the core diameter $d_{core}$ can consequently be up to 30 μm. In a lattice structure 10 with an expansion diameter $D_{exp}$ of 3.5 mm, a greater visibility factor f of up to approx. 0.07 is possible.

A visibility factor f of 0.08 can be used if the width ratio $R_{GS}$ is low or the wire diameter $d_{wire}$ high.

Selection of the suitable visibility factor f, results in a percentage proportion of the volume of core material 11a in relation to the overall volume of the wire 11. Preferably, the volumetric proportion of the core material 11a is between 13% and 32% in the case of a visibility factor of 0.05 and between 25% and 75% in the case of a visibility factor of 0.08. More particularly, with a visibility factor f of between 0.05 und 0.06, the volumetric proportion of the core material 11a can be between 20% and 30%, more particularly between 25% and 30%. With a visibility factor f of between 0.06 und 0.08, the volumetric proportion of the core material of the core material 11a is preferably between 25% and 45%, more particularly between 30% and 40%.

Applicable for all examples of embodiment of the invention is that through the use of a single wire 11 with a superelastic jacket material 11b, a lattice structure 10 can be formed that expands well and can be packed into miniaturised feeding systems and is also easily visible through the core material 11a that is visible under X-ray.

The particular challenge consists in producing the lattice structure by way of only a single wire 11. Single wire production requires the formation of loops 15 at the longitudinal ends 14 of the lattice structure 10. In the area of the loops 15, the wire 11 is subject to very great expansion (up to 8%, sometimes more), which when using conventional wire materials, for example cobalt-chromium alloys, can lead to plastic deformation of the wire 11 during compression of the lattice structure 10, so that at the longitudinal ends 14 the lattice structure 10 would no longer expand by itself. Instead, after implantation, the longitudinal ends 14 would remain bent radially inwards (cigar shape of the lattice structure 10) and could thereby encourage the formation of thrombi.

The superelastic jacket material 11b, envisaged in the invention, which in particular comprises nitinol, withstands such expansion. However, a precondition is also that the jacket material 11b has a corresponding thickness h in relation to the overall diameter of the wire 11. To this extent it is a question of the diameter and volume ratio between the core material 11a and the jacket material 11b.

In devices according to the invention, because of the superelastic jacket material 11b and its ratio to the X-ray visible core material 11a, the loops 15 have good elastic expansion properties and are also easily visible under X-rays. The positioning of the device in a blood vessel can therefore be easily monitored, which is also the case if the loops 15 have no additional X-ray marker sleeves 17.

In this context it has been shown that for the following wire diameters $d_{wire}$ the following core diameters $d_{core}$ are preferred:

For $d_{wire}$=45 μm: $d_{core}$=24.6 μm
For $d_{wire}$=50 μm: $d_{core}$=27.4 μm or 31.6 μm.
For $d_{wire}$=55 μm: $d_{core}$=30.1 μm or 34.8 μm.

A wire 11 with a wire diameter $d_{wire}$ of 50 μm is preferably used for lattice structures 10 with an expansion diameter $D_{exp}$ of between 2.5 mm and 5.0 mm.

For lattice structures 10 with an expansion diameter $D_{exp}$ between 2.5 mm and 3.0 mm, a wire 11 with a wire diameter $d_{wire}$ of 45 μm can also be used.

For lattice structures 10 with an expansion diameter $D_{exp}$ between 4.5 mm and 5.0 mm, a wire 11 with a wire diameter $d_{wire}$ of 55 μm can also be used.

The preferred thickness h of the jacket material is calculated as follows:

$$h=(d_{wire}-d_{core})/2$$

The jacket material 11b consequently has a thickness h, which for the above-described, preferred wire diameter $d_{wire}$ is at least 9 μm (with $d_{wire}$=50 μm and $d_{core}$=31.6 μm) and at most 12.4 μm (with $d_{wire}$=55 μm and $d_{core}$=30.1 μm).

With regard to the mesh number n, it is preferably envisaged that lattice structures 10 with an expansion diameter $D_{exp}$ of between 2.5 mm and 7.0 mm preferably have around 6 to 16 meshes 12 per mesh ring 13.

Lattice structures 10 with an expansion diameter $D_{exp}$ between 2.5 mm and 3.5 mm preferably have 6 or 8 meshes 12 per mesh ring 13. In the case of lattice structures 10 with an expansion diameter $D_{exp}$ between 3.5 mm and 5.0 mm, mesh rings 13 can each be provided with 6 or 8 or 10 or 12 meshes.

Lattice structures 10 with an expansion diameter $D_{exp}$ of between 5.0 mm and 7.0 mm preferably have a mesh number n of 8 or 10 or 12 or 14 or 16.

14

REFERENCE NUMBERS

10 Lattice structure.
11 Wire
11a Core material
11b Jacket material
12 Meshes
13 Mesh ring
14 Longitudinal end
15 Loop
16 Connection element
17 X-ray marker sleeve
18 Intersection
$D_{exp}$ Expansion diameter
$D_{comp}$ Compression diameter
$d_{core}$ Core diameter
$d_{wire}$ Wire diameter
b Mesh width
f Visibility factor
h Thickness of the jacket material 11b
$R_{GS}$ width ratio
α Braid angle
β Mesh angle
n Mesh number
φ Percent by volume

The invention claimed is:
1. A medical device comprising:
a radially self-expandable lattice structure made of a single wire interwoven with itself, the wire having a superelastic jacket material and a core material visible under X-ray, the wire forming meshes of the lattice structure divided into one or more tubular sections,
wherein the lattice structure includes a plurality of directly neighboring meshes in a circumferential direction of the lattice structure to form a mesh ring,
wherein in a fully self-expanded state, a core diameter ($d_{core}$) of the lattice structure equals a visibility factor (f) multiplied by a ratio of an expansion diameter $D_{exp}$ over a mesh number (n) of the mesh ring, expressed as $d_{core}$=f·($D_{exp}$/n), wherein the visibility factor varies in a range from 0.05 to 0.08,
wherein the expansion diameter is in a range between 2.5 mm and 7 mm, and wherein the lattice structure includes 6 or 8 meshes per mesh ring in case of the expansion diameter $D_{exp}$ being between 2.5 mm and 3.5 mm,
wherein the lattice structure includes 6 or 8 or 10 or 12 meshes per mesh ring in case of the expansion diameter $D_{exp}$ being between 3.5 mm and 5.0 mm, and
wherein the lattice structure includes 8 or 10 or 12 or 14 or 16 meshes per mesh ring in case of the expansion diameter $D_{exp}$ being between 5.0 mm and 7.0 mm.
2. The medical device according to claim 1, wherein a width ratio between the expansion diameter and the mesh number is one of,
between 0.3 mm and 0.5 mm, corresponding to the expansion diameter being between 2.5 mm and 3.5 mm, or
between 0.35 mm and 0.7 mm, corresponding to the expansion diameter being between 3.5 mm and 7 mm.
3. The medical device according to claim 1, wherein a braid angle of the lattice structure is between 60° and 70°.
4. The medical device according to claim 1, wherein a wire diameter of the wire is one of,
between 40 μm and 55 μm, corresponding to the expansion diameter being between 2.5 mm and 3.5 mm, or between 45 µm and 65 µm, corresponding to the expansion diameter being between 3.5 mm and 7 mm.

5. The medical device according to claim 1, wherein the superelastic jacket material has a thickness of at least 10 µm.

6. The medical device according to claim 1, wherein a volume of the core material constitutes a percentage proportional to an overall volume of the wire selected from one of, between 13% and 32%, corresponding to the visibility factor being 0.05, or between 25% and 45%, corresponding to the visibility factor being 0.08.

7. The medical device according to claim 1, wherein the lattice structure in a fully compressed state has a compression diameter of at most 0.7 mm.

8. The medical device according to claim 1, wherein the lattice structure has closed loops at each of two axial longitudinal ends.

9. The medical device according to claim 1, wherein longitudinal ends of the lattice structure are widened in a funnel shape.

10. The medical device according to claim 1, wherein the core material comprises one of platinum, a platinum alloy, tantalum, or a tantalum alloy.

11. The medical device according to claim 1, wherein the superelastic jacket material comprises a nickel-titanium alloy.

12. The medical device according to claim 1, further comprising a catheter, wherein in a compressed state, the medical device is configured and arranged in the catheter in a longitudinally displaceable manner.

13. The medical device according to claim 12, wherein the medical device is one of detachably connectable, firmly connectable, or connected to a transport wire.

14. The medical device according to claim 12, wherein the catheter has an inner diameter of at most 0.7 mm.

15. A medical device comprising:

a radially self-expandable lattice structure made of a single wire interwoven with itself, the wire having a superelastic jacket material and a core material visible under X-ray, the wire forming meshes of the lattice structure divided into one or more tubular sections, wherein the lattice structure includes a plurality of directly neighboring meshes in a circumferential direction of the lattice structure to form a mesh ring, wherein in a fully self-expanded state, a core diameter ($d_{core}$) of the lattice structure equals a visibility factor (f) multiplied by a ratio of an expansion diameter $D_{exp}$ over a mesh number (n) of the mesh ring, expressed as $d_{core} = f \cdot (D_{exp}/n)$, wherein the visibility factor varies in a range from 0.05 to 0.08, wherein a width ratio between the expansion diameter and the mesh number is one of, between 0.3 mm and 0.5 mm, corresponding to the expansion diameter being between 2.5 mm and 3.5 mm, or between 0.35 mm and 0.7 mm, corresponding to the expansion diameter being between 3.5 mm and 7 mm, wherein the expansion diameter is in a range between 2.5 mm and 7 mm, wherein the lattice structure includes 6 or 8 meshes per mesh ring in case of the expansion diameter $D_{exp}$ being between 2.5 mm and 3.5 mm, wherein the lattice structure includes 6 or 8 or 10 or 12 meshes per mesh ring in case of the expansion diameter $D_{exp}$ being between 3.5 mm and 5.0 mm, and wherein the lattice structure includes 8 or 10 or 12 or 14 or 16 meshes per mesh ring in case of the expansion diameter $D_{exp}$ being between 5.0 mm and 7.0 mm.

16. The medical device according to 15, wherein a wire diameter of the wire is one of, between 40 µm and 55 µm, corresponding to the expansion diameter being between 2.5 mm and 3.5 mm, or between 45 µm and 65 µm, corresponding to the expansion diameter being between 3.5 mm and 7 mm.

17. The medical device according to claim 15, wherein a wire diameter ($d_{wire}$) of the wire is at least 60 µm and a thickness of the superelastic jacket material is at least 15 µm.

18. The medical device according to claim 15, wherein a volume of the core material constitutes a percentage proportional to an overall volume of the wire selected from one of, between 20% and 30%, corresponding to the visibility factor being 0.05, or between 30% and 42%, corresponding to the visibility factor being 0.08.

19. A medical device comprising:

a radially self-expandable lattice structure made of a single wire interwoven with itself, the wire having a superelastic jacket material and a core material visible under X-ray, the wire forming meshes of the lattice structure divided into one or more tubular sections, wherein the lattice structure includes a plurality of directly neighboring meshes in a circumferential direction of the lattice structure to form a mesh ring, wherein in a fully self-expanded state, a core diameter ($d_{core}$) of the lattice structure equals a visibility factor (f) multiplied by a ratio of an expansion diameter $D_{exp}$ over a mesh number (n) of the mesh ring, expressed as $d_{core} = f \cdot (D_{exp}/n)$, wherein the visibility factor varies in a range from 0.05 to 0.08, wherein a width ratio between the expansion diameter and the mesh number is one of, between 0.4 mm and 0.5 mm, corresponding to the expansion diameter being between 2.5 mm and 3.5 mm, or between 0.38 mm and 0.7 mm, corresponding to the expansion diameter being between 3.5 mm and 7 mm, and wherein a volume of the core material constitutes a percentage proportional to an overall volume of the wire selected from one of, between 25% and 30%, corresponding to the visibility factor being 0.05, or between 35% and 42%, corresponding to the visibility factor being 0.08, wherein the expansion diameter is in a range between 2.5 mm and 7 mm, wherein the lattice structure includes 6 or 8 meshes per mesh ring in case of the expansion diameter Dex being between 2.5 mm and 3.5 mm, wherein the lattice structure includes 6 or 8 or 10 or 12 meshes per mesh ring in case of the expansion diameter Dem being between 3.5 mm and 5.0 mm, and wherein the lattice structure includes 8 or 10 or 12 or 14 or 16 meshes per mesh ring in case of the expansion diameter Dem being between 5.0 mm and 7.0 mm.

* * * * *